United States Patent [19]

Coleman et al.

[11] Patent Number: 5,200,471

[45] Date of Patent: Apr. 6, 1993

[54] BIOMOLECULES COVALENTLY IMMOBILIZED WITH A HIGH BOUND SPECIFIC BIOLOGICAL ACTIVITY AND METHOD OF PREPARING SAME

[75] Inventors: Patrick L. Coleman; Dean S. Milbrath; Margaret M. Walker, all of St. Paul, Minn.

[73] Assignee: Minnesota Mining and Manufacturing Company, St. Paul, Minn.

[21] Appl. No.: 609,436

[22] Filed: Nov. 5, 1990

[51] Int. Cl.⁵ .................... C08F 26/10; A61K 31/395
[52] U.S. Cl. ............................. 525/326.9; 424/78.08; 424/78.22; 424/78.23; 424/78.28; 424/78.29
[58] Field of Search .......................... 525/326.9, 326.9; 424/78.08, 78.22, 78.23, 78.28, 78.29

[56] References Cited

U.S. PATENT DOCUMENTS

| | | | |
|---|---|---|---|
| 3,925,267 | 12/1975 | Coupek et al. | 260/2.5 R |
| 4,070,348 | 1/1978 | Kraemer et al. | 260/79.3 |
| 4,104,363 | 8/1978 | Vozka et al. | 423/338 |
| 4,190,713 | 2/1980 | Kraemer et al. | 521/149 |
| 4,440,903 | 4/1984 | Golstein et al. | 525/54.1 |
| 4,511,694 | 4/1985 | Krämer et al. | 525/54.1 |

(List continued on next page.)

FOREIGN PATENT DOCUMENTS 0392735 4/1989 European Pat. Off. .
0392783 4/1990 European Pat. Off. .
0432629 12/1990 European Pat. Off. .

OTHER PUBLICATIONS

Lehninger, *Biochemistry*, 2nd Ed., p. 162 (1975).
Hannibal-Friedrich et al., "Immobilization of β-Galactosidase, Albumin, and γ-Globulin on Epoxy-Activated Acrylic Beads", Biotech. Bioengineer, vol. XXII, pp. 157-175, (1980).
Smalla et al., "Influence of Salts on the Covalent Immobilization of Proteins to Modified Copolymers of 2-Hydroxyethyl Methacrylate with Ethylene Dimethacrylate", Biotech. Appl. Biochem. 10, pp. 21-31, (1988).

Coleman et al., "Immobilization of Protein A at High Density or Azlactone-Functional Polymeric Beads and Their Use in Affinity Chromatography", J. Chromatogr. 512, pp. 345-363, (1990).
Turkova et al., "Hydroxyalkyl Methacrylate Gels Derivatized With Epichlorohydrin as Supports for Large-Scale and High-Performance Affinity Chromatography," J. Chromatogr. 215, pp. 165-179, (1981).
Rasmussen et al., "Polyazlactones" *Encyclopedia of Polymer Science and Engineering*, 2nd Ed., vol. 11, pp. 558-571, (1989).
Nakamura et al., "Preparation of Adsorbents for Affinity Chromatography Using Tskgel Tresyl-Toyopearl 65OM," J. Chromatogr. 478, pp. 159-167, (1989).
Sterogene, "Coupling Chemistry Actigel-ALD/Actigel-ALD Superflow," Sterogene Bioseparations Product Information Sht, Sterogene Bioseparations, Arcadia, Ca. (1990).
Eupergit Product Literature, "The New Matrix for Immobilization," Accurate Chemical & Scientific Corp., Westbury, N.Y., (1987).
Wehnert et al., "Glucose Oxidase Immobilized on Eup-

(List continued on next page.)

*Primary Examiner*—Thurman K. Page
*Assistant Examiner*—Raj Bawa
*Attorney, Agent, or Firm*—Gary L. Griswold; Walter N. Kirn; John H. Hornickel

[57] ABSTRACT

A biologically active adduct support, prepared from an azlactone-functional polymeric support and biomolecules covalently immobilized thereon, is disclosed. The biomolecules are covalently immobilized in the presence of polyanionic salt using a method which achieves both high density and optimized bound specific biological activity. Preferably, the immobilization occurs in the presence of an azlactone quencher.

16 Claims, 1 Drawing Sheet

U.S. PATENT DOCUMENTS

| | | |
|---|---|---|
| 4,563,490 | 1/1986 | Stol et al. ............................... 524/24 |
| 4,582,860 | 4/1986 | Bigwood et al. ...................... 521/56 |
| 4,704,366 | 11/1987 | Juarez-Salinas et al. ........... 436/501 |
| 4,710,525 | 12/1987 | Krämer et al. ....................... 523/201 |
| 4,737,560 | 4/1988 | Heilmann et al. .................. 526/304 |
| 4,775,714 | 10/1988 | Hermann et al. .................. 525/54.1 |
| 4,839,419 | 6/1989 | Kraemer et al. .................... 525/54.1 |
| 4,871,824 | 10/1989 | Heilmann et al. .................. 526/304 |
| 4,929,556 | 5/1990 | Cheng et al. ........................ 435/180 |
| 4,933,435 | 6/1990 | Ngo ...................................... 530/413 |
| 4,981,933 | 1/1991 | Fazio et al. .......................... 526/260 |

OTHER PUBLICATIONS ergit C and CPG-10, A Comparison", Biotech Letters, vol. 7, No. 11, pp. 817–830, (1985).

Harlow et al., "Antibodies—A Laboratory Manual," Cold Spring Harbor Laboratory, Chapter 13, pp. 536–537, (1988).

Zemanova et al., "Effect of the Nature of Proteins on Their Coupling to Different Epoxide-Containing Supports," *Enzyme Microb. Technol.*, vol. 3, pp. 229–232 (1981).

FIG.1

BIOMOLECULES COVALENTLY IMMOBILIZED WITH A HIGH BOUND SPECIFIC BIOLOGICAL ACTIVITY AND METHOD OF PREPARING SAME

FIELD OF THE INVENTION

This invention relates to the use of inorganic and organic polyanionic salts in aqueous buffered media to enhance bound specific biological activity of covalently immobilized biologically active materials on azlactone-functional polymeric supports.

BACKGROUND OF THE INVENTION

A wide variety of chemical reactions has been proposed for immobilizing proteins on solid supports.

There are three critical requirements for covalent immobilization of proteins on solid supports.

Speed of covalent immobilization facilitates processing conditions. Density of immobilized proteins on the support determines the quantity of protein potentially available for subsequent reaction. Bound activity of the immobilized protein determines the quantity of the protein actually available for subsequent reaction.

It has been known in the art that some activated polymeric supports will bind more protein under highly ionic immobilization conditions. For example, Hannibal-Friedrich et al. report that binding of albumin and gamma-globulin to oxirane-acrylic beads are maximized in the presence of a 1.0 molar aqueous potassium phosphate solution at pH at 7.6. But the immobilization required a minimum of 5 hours. (Hannibal-Friedrich et al., Biotech. Bioengineer. 22 (1980) p. 157 et seq.)

It is also known that the covalent immobilization of many useful proteins is enhanced in the presence of sulfate ions. This effect was first noted in reference to oxirane-functional methacrylate copolymers and hydroxyethyl methacrylate polymers. (Smalla et al. Biotech. Appl. Biochem. 10 (1988) p. 21).

The art has previously reported the density of immobilized protein on the support and the amount of activity bound on the support, in order to reveal efficacy of an immobilization process.

If biologically active material were inexpensive and easy to prepare and handle, one could maximize bound biological activity by maximizing the density of the biologically active material immobilized on the support. That processing regimen could ignore economic considerations.

Economic considerations also suffer from slow immobilization processes. Protein coupling to activated supports such as oxirane (epoxide), cyanogen bromide, activated thiol, aldehyde, and hydrazide required immobilization of at least 5 and as much as 72 hours; c.f. Coleman et al., J. Chromatogr. 512 (1990) p. 360 with respect to References 19-24. For example, although described as highly universal and possible at reaction times from 0.5-40 hours, each experiment reported in U.S. Pat. No. 4,775,714 (Hermann et al.) required immobilization for at least 5 hours. Thus, even with inorganic salts like ammonium sulfate or sodium sulfate present during immobilization, the covalent coupling of protein to the support may result in acceptable protein density and bound biological activity; but the immobilization process is slow.

Others have taught the use of high concentrations of polyvalent anion in a two step reaction to immobilize proteins on a solid, nonreactive support. U.S. Pat. No. 4,839,419 (Kraemer et al.) discloses the use of sulfates, phosphates, pyrophosphates, carbonates, chromates, citrates and tartrates to adsorb the protein to a nonreactive support followed by a crosslinking step with a reagent such as glutaraldehyde to immobilize the protein adsorbed on the support. Another process employs reactive supports and dispenses with the need for the protein crosslinking step. Examples 3 and 4 report bound biological activity and activity yields of 55% and 61%, respectively, for enzyme immobilizations lasting for 72 hours and and 8 hours, respectively, using a bead support having epoxy functionality.

Azlactone-functional copolymer beads, such as those described in U.S. Pat. Nos. 4,737,560 and 4,871,824 and European Patent Publication 0 392 735 (all Heilmann et al.), have a high capacity for immobilizing protein densely while retaining significant bound biological activity. This capacity is largely independent of the degree of azlactone functionality, within the range of 1-3 meq/g of mass of beads. Further, as described in each Heilmann et al. patent or publication identified above, the attaching reaction of an azlactone-functional polymeric support with a protein in an aqueous media is very rapid, typically reaching half of the maximum amount of coupling within about five minutes after reaction initiation and completion in less than three hours.

The immobilization reactions reported in each Heilmann et al. patent or publication identified above use a low concentration (e.g., 25 mM) of phosphate buffer solution, with or without the presence in physiological concentrations of an inorganic monoanionic salt, NaCl, to carry out the immobilization. Immobilization is complete within not more than three hours.

As is conventional for protein immobilization, the immobilization in each Heilmann et al. process is followed by quenching of the remaining azlactone-functional groups on the polymeric support by reaction with an azlactone quencher, such as ethanolamine.

SUMMARY OF THE INVENTION

The present invention provides a method to economically and rapidly retain bound specific biological activity during covalent immobilization of a biologically active material.

The difference between bound biological activity and bound specific biological activity is critical to the economics of immobilization techniques.

"Bound biological activity" describes the amount of biologically active material remaining active and available for further reaction after being immobilized on a support. Bound biological activity is expressed in terms of units of activity per mass or volume of support.

"Bound specific biological activity" describes the amount of bound biological activity as a function of the total amount of biologically active material immobilized. Bound specific biological activity is expressed as a ratio of moles or units of active biologically active material to moles or mass of total biologically active material immobilized.

Bound specific biological activity identifies the efficiency of the immobilization process and the quality of the biologically active material immobilized. The present invention uses a method to optimize the efficiency of immobilization, in order to minimize the waste of immobilizing biologically active material that fails to retain biological activity. The present invention uses a method to optimize the quality of the biologically active material immobilized.

The prior art has emphasized sheer quantity of density and bound biological activity to show utility of immobilization. The present invention has found the same bound biological activity as reported in the art can be achieved with less density of immobilization than needed in the prior art techniques. More importantly, once bound specific biological activity is optimized, immobilizations of the same density as used in the prior art techniques can achieve more bound biological activity.

Optimized bound specific biological activity is achieved by covalently immobilizing biologically active material on an azlactone-functional polymeric support in the presence of polyanionic salts in an aqueous buffered medium. Because azlactone-functional polymeric supports react rapidly and under facile processing conditions, the method of the present invention produces a biologically active support satisfying the three critical requirements of covalent immobiliztion described above without economic waste of biologically active material.

A method for the covalent immobilization of biologically active material on azlactone-functional polymeric supports is provided. The method comprises dissolving biologically active material into a highly ionic buffered salt solution to form a biologically active material solution; and mixing said biologically active material solution with azlactone-functional polymeric supports to form within three hours a biologically active adduct support having a bound specific biological activity of at least ten percent greater than a biologically active adduct support formed in buffered saline solution of a physiological concentration. The highly ionic buffered salt solution comprising a polyanionic salt having a concentration of from about 0.5M to about solubility limit of said polyanionic salt.

The present invention yields a biologically active adduct support having units of the formula wherein
$R^1$, $R^2$, $R^3$, and n are as previously defined,
n=0 or 1,
X is —O—, —S—, —NH—, or —NR$^4$ wherein R$^4$ is alkyl or aryl, and
G is the residue of biologically active material and has a bound specific biological activity of at least ten percent greater than a biologically active adduct support of said formula formed in buffered saline solution of a physiological concentration.

One embodiment of the present invention uses polyanionic salts in aqueous media to covalently immobilize biologically active materials on azlactone-functional polymeric supports, resulting in optimized bound specific biological activity. The polyanionic salts may be inorganic or organic.

A second embodiment of the present invention uses either inorganic polyanionic salts or organic polyanionic salts and an azlactone quencher in aqueous media to covalently immobilize biologically active materials on azlactone-functional polymeric supports. Even though a quencher is present competing with protein for reactive sites, unexpectedly, both optimal density and optimal bound specific biological activity have been found.

Both of the embodiments of the present invention involve using polyanionic salts to produce an immobilization that is very rapid and facile.

The present invention solves the problems of using activated supports that are not azlactone-functional by providing a method of immobilization that is very rapid and optimizes bound specific biological activity achieved.

The present invention also advances the art of using azlactone-functional polymeric supports by providing a method of optimizing bound specific biological activity for covalently immobilized biologically active material.

In this application:

"azlactone-functional polymeric support" means an article comprising an azlactone-functional polymer or an azlactone-functional polymer coated on at least one surface of a substrate as described in U.S. Pat. No. 4,871,824 and European Patent Publication 0 392 735, the disclosures of which are incorporated herein by reference (hereinafter collectively Heilmann et al.);

"azlactone" means 2-oxazoline-5-one groups of Formula I and 2-oxazin-6-one groups of Formula II:

I   II

"biologically active materials" refers to biomolecules that are biochemically, immunochemically, physiologically, and/or pharmaceutically active, such as proteins, antibodies, antigens, enzymes, cofactors, lectins, hormones, receptors, coagulation factors, histones, cell receptors, and cell surface antigens;

"inorganic polyanionic salts" refers to inorganic polyacids and salts thereof that are soluble in aqueous buffered media used in immobilization reactions, such as sulfates, phosphates, pyrophosphates, pyrosulfates, arsenates, and borates, as salts of alkali metal, alkaline earth metals, and ammonium.

"organic polyanionic salts" refers to organic polyacids and salts thereof that are soluble in aqueous buffered media used in immobilization reactions, such as citrates, tartrates, malonates, EDTA, and succinates of the same cations as inorganic polyanionic salts;

Polyanionic salts means at least one inorganic polyanionic salt or at least organic polyanionic salts.

"highly ionic buffered salt solution" refers to at least one inorganic or organic polyanionic salt and a buffering agent dissolved in water; and "azlactone quencher" refers to an amine-containing, alcohol-containing, or thiol-containing compound which also reacts with azlactone-functional polymeric supports.

The present invention is further described in the following Embodiments of the Invention with reference to the Drawing.

EMBODIMENTS OF THE INVENTION

Azlactone-Functional Polymeric Supports

The embodiments of the present invention can employ any of the azlactone-functional polymeric supports disclosed in Heilmann et al., (specifically in U.S. Pat. No. 4,871,824 or European Patent Publication 0 392 735). In this application with respect to azlactone-functional polymeric supports:

"acryloyl" means not only 1-oxo-2-propenyl but also 1-oxo-2-methyl-2-propenyl resulting from methacryloylation reactions;

"alkyl" means the monovalent residue remaining after removal of a hydrogen atom from a saturated linear or branched chain hydrocarbon having 1 to 14 carbon atoms;

"aryl" means the monovalent residue remaining after removal of one hydrogen atom from an aromatic or heteroaromatic compound which can consist of one ring or two fused or catenated rings having 5 to 12 ring atoms which can include up to 3 heteroatoms selected from S, N, and nonperoxidic O. The carbon atoms can be substituted by up to three halogen atoms, $C_1$–$C_4$ alkyl, $C_1$–$C_4$ alkoxy, N,N-di($C_1$–$C_4$ alkyl)amino, nitro, cyano, and $C$–$C_4$ alkyl carboxylic ester;

"arenyl" means the monovalent residue remaining after removal of a hydrogen atom from the alkyl portion of a hydrocarbon containing both alkyl and aryl groups having 6 to 26 carbon and heteroatoms (wherein the heteroatoms are up to 3 S, N, and nonperoxidic O atoms);

"parts" means parts by weight unless otherwise specified;

"carboxylate" means wherein M is hydrogen, ammonium, or an alkali metal such as Li, Na, or K;

"macroporous" refers to crosslinked polymers in which the level of crosslinker or difunctional monomers is greater than 20 parts, with no polymer non-solvent or porogen utilization being required; and "gel-type" refers to crosslinked polymers in which the level of crosslinkers or difunctional monomers is less than 20 parts.

Structures and formulae depicted between parentheses are partial structures of polymers.

The present invention uses azlactone-functional polymeric supports having on at least one of their surfaces units of Formula V:

wherein
$R^1$ is H or $CH_3$,
$R^2$ and $R^3$ independently can be an alkyl group having 1 to 14 carbon atoms, a cycloalkyl group having 3 to 14 carbon atoms, an aryl group having 5 to 12 ring atoms, an arenyl group having 6 to 26 carbon and 0 to 3 S, N, and nonperoxidic O heteroatoms, or $R^2$ and $R^3$ taken together with the carbon to which they are joined can form a carbocyclic ring containing 4 to 12 ring atoms, and
n is an integer 0 or 1.

These supports may be crosslinked azlactone-functional polymeric beads or they may be solid substrates coated on at least one surface with a layer of an azlactone-functional polymer. This layer may have a thickness in the range of 1 nanometer to 5 mm. Useful solid substrates include inorganic solids such as glass, ceramics, unfired metal and nonmetal oxides, clays, zeolites, and organic polymers.

Covalent immobilization according to the present invention results in adduct supports having the formula wherein
$R^1$, $R^2$, $R^3$, and n are as previously defined,
X can be —O—, —S—, —NH—, or —$NR^4$ wherein $R^4$ can be alkyl or aryl, and
G is the residue of HXG which performs the adsorbing, complexing, catalyzing, separating, or reagent function of the adduct supports.

HXG can be biologically active material.

Of the various azlactone-functional polymeric supports disclosed in Heilmann et al., polymeric beads having azlactone functionality identified in Formula I above are desired. Of the various azlactone-functional polymeric beads disclosed in Heilmann et al, a copolymer bead of vinyldimethylazlactone (VDM) and methylene-bis-acrylamide (MBA), in a ratio in a range from about 20:80 VDM:MBA to about 05:95 VDM:MBA is presently preferred.

Azlactone-functional polymeric supports may be prepared according to any of the methods disclosed in Heilmann et al.

The azlactone-functional polymeric supports used by this invention are provided by one of several processes:

PROCESS I

Two-step Reverse Phase Suspension Polymerization

The polymer and adduct supports of Process I of the invention can be provided according to the process depicted by Chemical Equations I, below.

CHEMICAL EQUATIONS (PROCESS I) I

N-acryloylamino acid salt III step 1 carboxylate-functional supports IV cyclization agent | step 2 azlactone-functional polymeric supports V functional material HXG | step 3 biologically active adduct supports VI

The crosslinked hydrophilic, azlactone-functional polymer beads of Formula V are prepared by a two-step process. In the first step the following group of monomers is subjected to a free radical polymerization reaction:

i) 0 to 89 molar parts of at least one water soluble monomer;

ii) 1 to 99.9 molar parts of at least one water soluble salt of N-(meth)acryloylamino acid; and iii) in the range of 0.1 to 99 molar parts, preferably 7 to 99, more preferably 10 to 99, and most preferably 30 to 99 molar parts, of at least one crosslinking monomer.

The product of the above polymerization reaction is the crosslinked, hydrophilic, carboxylate-functional supports of Formula IV. The second step of the process involves treating the carboxylate-functional supports with a cyclization agent to form the azlactone-functional polymeric supports.

The degree of hydrophilicity of the polymer support is largely determined by the amount of water soluble monomer employed, although some hydrophilicity is imparted by the crosslinker and by the functional groups created, i.e., amide-amide, amide-ester, or amide-thiolester with amine, alcohol, or thiol nucleophiles (HXG as defined above), by the ring-opening, azlactone/nucleophile reaction (step 3 of Chemical Equations I). Therefore, inclusion of a water soluble monomer is optional. Suitable water soluble monomers exhibit a solubility of at least 3 parts in 100 parts water. Preferred monomers include vinyl group-containing and acryloyl group-containing compounds. A representative list of such monomers includes acrylamide, methacrylamide, N,N-dimethylacrylamide, diacetoneacrylamide, N-vinylpyrrolidone, hydroxyethyl methacrylate, 2-acrylamido-2-methylpropanesulfonic acid and its salts, N-(3-methacrylamidopropyl)-N,N,N-trimethylammonium salts, N,N-dimethylaminoethyl methacrylate, acrylic acid, methacrylic acid, itaconic acid, and combinations thereof. Preferred water soluble monomers are N,N-dimethylacrylamide and N-vinylpyrrolidone.

The N-acryloylamino acid salt monomers include ammonium, sodium, potassium, and lithium salts of N-acryloylamino acids of Formula VII and are prepared by mixing (at <30° C.) equal molar quantities of aqueous solutions of, for example, ammonium hydroxide, sodium hydroxide, potassium hydroxide, or lithium hydroxide and the Formula VII compounds.

VII wherein $R^1$, $R^2$, $R^3$, and n are as previously defined.

The N-acryloylamino acid compounds are well-known and can be readily synthesized. For Formula VII compounds in which n=0, either the sodium salt of the appropriate amino acid can be acryloylated, for example, according to K. Huebner, et al., *Makromol. Chem.*, 11, 109 (1970) or, more efficiently, by the method described in U.S. Pat. No. 4,694,103 which involves the one-pot transformation of a ketone into an N-acryloylamino acid. For Formula VII compounds wherein n=1, a useful preparation is the transformation of 3,3-disubstituted acrylic acids as disclosed by D. I. Hoke, et al, *J. Polym. Sci.: Polym. Chem. Ed.*, 10, 3311 (1972).

Insolubilization is a necessary condition for easy removal of the support (e.g., beads) from the system. This is accomplished by inclusion of a monomer which contains a plurality of polymerizable groups and whose participation in a polymerization reaction results in the physical joining of polymer backbones or crosslinking. Crosslinking is also desirable in polymer-supported materials because the mechanical stability is generally substantially enhanced and some degree of control of bead size can be exercized by manipulation of the level of crosslinking, i.e., in general for a given polymerization condition, the greater the amount of crosslinker the smaller the bead size. The degree of crosslinking depends primarily on the intended use of the support material. In all instances the polymers are insoluble in all solvents and possess a molecular weight which is essentially infinite. For many applications requiring fairly high capacities and involving relatively small solute reaction partners which can diffuse into the swollen polymer support, low to moderate degrees of crosslinking are desired. According to D. C. Sherrington, *Br. Polym. J.*, 16, 164 (1984), these crosslinked swellable supports (referred to as "gel-type" polymers) result from inclusion of from 1 to 20 parts of a multifunctional monomer. For certain applications requiring low degrees of physical expansion due to swelling and which can tolerate lower capacities, (as in certain operations conducted in confined flow systems such as chromatographic columns or column reactors), highly crosslinked hydrophobic systems resulting from copolymerization of more than 20 parts of a multifunctional monomer are utilized. These are so-called "macroporous" polymers which are generally regarded as being non-swelling, and solute/support reactions occur primarily at the solvent/support interface. Applications of these supports may involve large solutes, e.g., biomacromolecules, which cannot, because of their large size, diffuse into the polymer network.

In order to achieve a condition of low swelling in aqueous buffered media, a substantially greater concentration of multifunctional monomer is necessary than the 20 parts commonly utilized in the so-called non-swelling, hydrophobic, macroporous resins described above. This may be a consequence of the utilization of these hydrophilic supports in water and the high degree of hydrophilicity imparted by the multifunctional monomers themselves, as they consist largely of highly polar functional groups.

To prepare azlactone-functional polymeric supports, hydrophilic comonomers and hydrophilic crosslinkers can be utilized. Swelling of beads so produced varies inversely with the amount of multifunctional crosslinker present. Polymer supports (e.g., beads packed together) with a low degree of swelling (less than 3 times the unswelled volume) generally require substantially greater than 20 parts of difunctional crosslinker.

Surprisingly, there can still be a relatively low degree of swelling and high binding capacities of polymer beads in water with more than 5 mol % crosslinker (in hydrophilic systems). Such beads are useful as complexing agents, catalysts, polymeric reagents, chromatographic supports, and enzyme-, other protein-, and other biomacromolecule-bearing supports.

To achieve polymer beads with a low degree of swelling and still maintain high binding capacity, substantially greater amounts of crosslinker are required in hydrophilic systems. Such polymer beads are particularly useful in chromatographic applications and column reactors.

Suitable multifunctional crosslinking monomers include ethylenically unsaturated ($\alpha,\beta$-unsaturated) esters such as ethylene diacrylate, ethylene dimethacrylate, trimethylolpropane triacrylate and trimethacrylate, and $\alpha,\beta$-unsaturated amides, such as methylenebis(acrylamide), methylenebis(methacrylamide), N,N'-diacryloyl-1,2-diaminoethane, N,N'-dimethacryloyl-1,2-diaminoethane, and reaction products of 2-alkenyl azlactones and short chain diamines such as those represented by Formulae VIII and IX:

The crosslinking monomers should be at least sparingly soluble in water but need not be as water soluble as defined for the water soluble monomer component. This is not generally a problem for the preparation of gel-type polymers because relatively small proportions of the crosslinking monomers are utilized with relatively large quantities of water solvent, and often the water soluble monomer component, especially N,N-dimethylacrylamide and N-vinylpyrrolidone, will facilitate solution of the crosslinking monomer. For macroporous polymers, however, in which the concentration of crosslinking monomer is greater than 20 parts it may be necessary to add a co-solvent which will facilitate dissolution of the crosslinking monomer. Suitable co-solvents include N,N-dimethylformamide, N,N-dimethylacetamide, N-methylpyrrolidone, and dimethylsulfoxide.

The technique of polymerization employed in PROCESS I is often referred to as "reverse-phase" or "inverse" suspension polymerization, and a general discussion of this technique is disclosed by M. Munzer, et al., "Suspension Polymerizations from Non-Aqueous Media", in "Polymerization Processes" edited by C. E. Schildknecht and I. Skeist, Wiley-Interscience, New York, pp. 123-124 (1977). The reversal of the normal suspension polymerization technique (in which water is the usual suspending medium) is necessary because the monomers of the present invention are soluble in water and therefore require a water immiscible suspending medium.

The primary purpose of the suspending medium, besides functioning as an inert medium for dispersion of the polymerizable phase, is to dissipate the heat generated in the polymerization reaction. An important characteristic of the suspending medium is its density. In order to obtain spherical polymer beads of uniform size, the beads, once formed, should not exhibit a tendency to sink or float in the suspending medium. Therefore, the suspending medium and aqueous phases should be of approximately the same density.

The actual polymerization occurs in individual droplets of water containing the dissolved monomers and initiator. The droplets are formed and maintained in the suspending medium by vigorous agitation, and the resultant beads, size and individuality (i.e., lack of aggregation) are controlled by the addition of various suspending agents which are surface active molecules that generally contain both hydrophobic and hydrophilic parts.

Step two of PROCESS I of the invention consists of conversion of the carboxylate-functional beads into azlactone-functional beads. This is accomplished using a cyclization agent (CA). A cyclization agent is a reagent that can react with the carboxylate-functional beads to form an intermediate adduct which is susceptible to intramolecular attack by the amide carbonyl group to form azlactone groups according to CHEMICAL EQUATIONS IA. This susceptibility is chiefly accomplished by forming a good leaving group (−O(CA) below) for the nucleophilic attack by the carbonyl.

CHEMICAL EQUATIONS IA wherein $R^1$, $R^2$, $R^3$, and n are as defined above.

(Structures and formulae depicted between parentheses are partial structures of polymers depicting side chains that actively participate in the cyclization reaction. Use of brackets has the usual meaning of chemical intermediates or activated complexes. Dotted lines mean partial bonds, and δ means partial ionic charges.)

Useful cyclization agents for transformation of the carboxylate-functional supports include, by way of example, acetic anhydride, trifluoroacetic anhydride, and alkyl chloroformates such as methyl, ethyl, and isopropyl chloroformates. Carbodiimides such as N,N'-dicyclohexylcarbodiimide can be effectively utilized but require an additional step of acidifying the carboxylate-functional supports to form carboxyl-functional supports which can then be cyclized to azlactone-functional supports using the carbodiimide reagent. To facilitate understanding of the cyclization step, the intermediates that would result by employing the aforementioned cyclization agents are depicted below in order of mention.

The progress of the cyclization reaction can be easily monitored by examination of the infrared spectrum of the polymer supports. Appearance of a carbonyl stretching absorption at about 1820 cm$^{-1}$ is evidence of azlactone groups. Indeed, one reason azlactone groups are so useful as linkages for covalent attachment to polymers is the ability to monitor reactions by observation of this infrared absorption, either the appearance of it in the synthesis of the azlactone-functional supports or the disappearance of it in the subsequent reaction with a functional material. This absorption is strong, very characteristic of azlactones, and located in a region of the infrared spectrum where essentially no other common absorptions are observed. This is a decided advantage over other linking functional groups such as the chloromethylphenyl and oxirane which lack these unique features in their infrared spectra. A convenient analytical method for monitoring attaching reactions really does not exist with these latter groups.

Because of its low cost, availability, and liquid state at cyclization temperatures, acetic anhydride is a preferred cyclization agent. Typically, the carboxylate-functional supports are covered with acetic anhydride, and the mixture is warmed at temperatures from 40°–100° C., preferably 80°–100° C., for a period of 2–24 hours. After the cyclization reaction, the polymer supports are filtered. What also makes acetic anhydride particularly preferred is that the by-product of cyclization, the alkali metal acetate salt, is fairly soluble in acetic anhydride and can easily be removed from the azlactone-functional supports. The supports can then be dried directly or, as is often conducted, subjected to a series of washing operations with non-reactive organic solvents such as acetone, toluene, ethyl acetate, heptane, and chloroform prior to drying.

PROCESS II

One Step Reverse Phase Suspension Polymerization

Polymeric supports of PROCESS II are provided according to the process depicted in CHEMICAL EQUATIONS II, below.

CHEMICAL EQUATIONS II (PROCESS II)

Alkenyl Azlactone
X

Azlactone-Functional Supports
V

This process is conducted by the same polymerization technique as that employed in PROCESS I, and employs the same water soluble monomers and crosslinkers. The major difference is in the utilization of an alkenyl azlactone monomer X instead of the N-acryloylamino acid salt III. The amounts of reactants can be the same as for PROCESS I except that azlactone replaces the salt of N-(meth)acryloylamino acid. This process advantageously provides azlactone-functional polymer supports V in a single step, as opposed to the two-step process of PROCESS I. Several aspects of this process are surprising in light of the prior art. First of all, the alkenyl azlactones X are fairly soluble in the suspending medium, yet they become readily incorporated in the polymer support (e.g., beads) without detrimental effects upon the polymerization process. Secondly, the azlactone ring is not hydrolyzed by the water in the aqueous phase during this polymerization process. After the polymerization process, the beads can be isolated, for example, by filtration, and subjected to a series of washing steps, if desired, and dried.

Useful azlactone monomers and their syntheses are described in U.S. Pat. No. 4,378,411 and in "Polyazlactones", Encyclopedia of Polymer Science and Engineering, Vol. 11, Second Edition, Wiley, N.Y., 1988, pp. 558–571, both of which are incorporated herein by reference, and include: 2-vinyl-4,4-dimethyl-2-oxazolin-5-one, 2-isopropenyl-4,4-dimethyl-2-oxazolin-5-one, 2-vinyl-4,4-diethyl-2-oxazolin-5-one, 2-vinyl-4-ethyl-4-methyl-2-oxazolin-5-one, 2-vinyl-4-dodecyl-4-methyl-2-oxazolin-5-one, 2-vinyl-4,4-pentamethylene-2-oxazolin-5-one, 2-vinyl-4-methyl-4-phenyl-2-oxazolin-5-one, 2-isopropenyl-4-benzyl-4-methyl-2-oxazolin-5-one, and 2-vinyl-4,4-dimethyl-1,3-oxazin-6-one.

Preferred azlactone monomers are 2-vinyl-4,4-dimethyl-2-oxazolin-5-one (which is commercially available from SNPE, Inc., Princeton, N.J.), 2-isopropenyl-4,4-dimethyl-2-oxazolin-5-one, and 2-vinyl-4,4-dimethyl-1,3-oxazin-6-one.

PROCESS III

Dispersion Polymerization

Polymeric supports of PROCESS III are provided by a polymerization process termed "dispersion polymerization", and in particular, by dispersion polymerization in organic media. In this process which is somewhat analogous to PROCESS II, the monomers and solvent are initially homogeneous. Shortly after polymerization begins, polymer separates as particles and the polymerization then continues in a heterogeneous manner. Polymeric "dispersants" or "stabilizers" are typically used to prevent aggregation of polymer particles during the polymerization process. Techniques for dispersion polymerization in non-aqueous media are well-known in the art, and are described in detail, for example, by K. E. J. Barrett in "Dispersion Polymerization in Organic Media", Wiley, N.Y., 1975. A dispersion polymerization technique which has proven advantageous for the preparation of azlactone-functional polymeric supports of PROCESS III is that described by Y. Almog, et al., *Brit. Polym. J.*, 1982, 131, which is incorporated herein by reference.

In general, azlactone-functional polymer supports of Formula V are prepared according to PROCESS III by subjecting to a free radical polymerization reaction the following group of monomers:
i) 1–100 molar parts of at least one alkenyl azlactone of Formula X;
ii) 0–99 molar parts of at least one crosslinking monomer; and
iii) 0–99 molar parts of at least one comonomer.

Suitable crosslinking monomers for use in this polymerization process include the ones useful for PROCESSES I and II. However, since water solubility is not a criterion in dispersion polymerization but rather solubility in the dispersing medium, other crosslinkers may be utilized such as, for example, divinyl compounds such as divinylbenzene.

Comonomers useful for the preparation of supports according to PROCESS III include the water soluble comonomers useful in PROCESSES I and II, but again include additional comonomers which are not water soluble. Virtually any free radically polymerizable monomer may be utilized as comonomer subject to the requirement that it have initial solubility in the dispersing medium.

Examples include: the vinyl aromatic monomers such as styrene, α-methylstyrene, 2- and 4-vinylpyridine; α,β-unsaturated carboxylic acids such as acrylic acid, methacrylic acid, itaconic acid, maleic acid, fumaric acid, and crotonic acid; α,β-unsaturated carboxylic acid derivatives such as methyl methacrylate, butyl methacrylate, 2-ethylhexyl methacrylate, ethyl acrylate, butyl acrylate, iso-octyl acrylate, octadecyl acrylate, cyclohexyl acrylate, tetrahydrofurfuryl methacrylate, phenyl acrylate, phenethyl acrylate, benzyl methacrylate, α-cyanoethyl acrylate, maleic anhydride, diethyl itaconate, acrylamide, methacrylonitrile, N,N-dimethylacrylamide, and N-butylacrylamide; vinyl esters of carboxylic acids such as vinyl acetate and vinyl 2-ethylhexanoate; vinyl halides such as vinyl chloride and vinylidene chloride; vinyl alkyl ethers such as methyl vinyl ether, 2-ethylhexyl vinyl ether, and butyl vinyl ether; olefins such as ethylene; N-vinyl compounds such as N-vinylpyrrolidone and N-vinylcarbazole; vinyl ketones such as methyl vinyl ketone; and vinyl aldehydes such as acrolein and methacrolein.

As is well known to one skilled in the art of dispersion polymerization, an inert diluent or dispersing medium must be chosen which will dissolve the monomer or monomer mixture but will precipitate the polymer as it forms. This presents a particular problem when preparing crosslinked polymers, since they are insoluble in all solvents. Therefore a dispersing medium must be chosen which will favor the separation of discrete particles during the polymerization process rather than formation of a crosslinked mass. A useful concept to aid in the determination of dispersing media or in choosing appropriate monomer mixtures which may be dispersion polymerized in a particular medium is the concept of solubility parameter. This concept and its relationship to dispersion polymerization is discussed in detail by Barrett, supra (Chapter 4). Tables of solubility parameter values for many solvents and some polymers, as well as methods for the estimation of solubility parameter values for polymers and copolymers, can be found in *Polymer Handbook*, J. Brandrup and E. H. Immergut, Editors, 2nd Edition, Wiley, New York, 1975, p. IV-337ff. In general, for a successful dispersion polymerization, the solubility parameter of the dispersing medium and of the polymer being formed should differ by at least about 1 to 1.5 solubility parameter units, preferably by 1.5 to 2 or more solubility parameter units. Therefore, for most monomer mixtures, solvents useful as dispersing media include nonpolar hydrocarbons such as pentane, hexane, petroleum ether, cyclohexane, and toluene, and the polar, hydroxylic solvents such as the alcohols methanol, ethanol, isopropanol, and t-butanol.

Initiators useful for PROCESS III include all free radical initiators which are soluble in the dispersing medium. Choice of the initiator will depend, as is well known in the art, upon the temperature at which the polymerization is conducted. Initiators useful at elevated temperatures, such as at 50° C. or higher, include azo compounds, such as azobisisobutyronitrile, and peroxides or hydroperoxides such as benzoylperoxide, di-t-butylperoxide, t-butylhydroperoxide, and cumene hydroperoxide. For lower temperature reactions, for example at room temperature, redox initiators may be utilized such as, for example, peroxides or hydroperoxides in combination with a tertiary amine. One such redox system is benzoyl peroxide/N,N-dimethylaniline. Initiators can be present in an amount in the range of 0.1 to 10 weight percent of the monomer composition, preferably 0.5 to 2.0 weight percent.

As mentioned above, the dispersion polymerization procedure of Almog, et al., has been used effectively for the preparation of azlactone-functional supports by PROCESS III. This procedure employs an alcohol as the dispersing medium, and azobisisobutyronitrile as the initiator. A polymeric stabilizer such as polyvinylpyrrolidone, poly(vinyl methyl ether), polyacrylic acid, or polyethyleneimine is used in conjunction with Aliquat 336 (Henkel Corporation) as cosurfactant. Again a surprising and unexpected result of this procedure is that azlactone-functional polymer supports, both crosslinked and noncrosslinked, may be prepared in one step in this hydroxylic medium without reaction of the alcohol solvent with the azlactone. Isolation involves a simple filtration, washing if desired, and drying.

While the beads prepared by the three processes described above all exhibit azlactone functionality on their surfaces, their physical properties may vary widely depending upon the process used for their preparation. The beads prepared via reverse phase suspension polymerizations are generally highly porous (i.e., 10 to 90 volume percent voids, preferably 20 to 75 volume percent voids), with large surface areas and pore volumes, and have a high density of reactive groups. These beads are useful for applications in which binding capacities are of relatively more importance than are reaction kinetics. Beads produced by dispersion polymerizations, on the other hand, are generally smaller in size and are much less porous, in some instances being virtually nonporous. With these beads, reaction kinetics are very fast, a characteristic which can be particularly useful in certain applications such as those requiring higher throughput rates.

PROCESS IV

Coating Solid Supports with Uncrosslinked Azlactone Polymers

As noted above, azlactone-functional polymeric supports can be in the form of beads. This is a physical form in which the supports possess great utility, particularly for uses such as packing chromatographic columns. However, the new materials are not restricted to the physical form of beads. We have found that certain soluble azlactone polymers (uncrosslinked) can also be coated on a number of substrates and they exhibit the same reactive azlactone functionality in these forms as they do as beads. Thus, these substrates may be used for reaction with functional materials. For example, nylon filtration membranes and glass surfaces can be coated with azlactone polymers of this invention, by dipping the object to be coated into a solution of the polymer and allowing the dipped object to dry. Similarly, particulate material, such as ceramics (e.g., zirconium oxide) or unreactive polymers, such as particles of polyethylene, can be coated with azlactone functional polymers. Other solution coating methods well known in the art may be used, such as for example spray coating and knife coating, depending upon the physical form of the substrate.

Similar results have been obtained when silica beads were used as a substrate upon which azlactone-functional polymers were coated on substrates. This kind of bead is commonly used as a packing in chromatographic columns. Likewise, using glass beads of controlled pore size, again a common column packing medium, significantly improved protein binding and covalent binding have been found when using an azlactone-functional coating. Particular advantages of azlactone-functional polymeric supports of PROCESS IV are their incompressibility and almost complete lack of swelling.

The azlactone-functional polymers useful for preparing coatings on solid substrates are well known in the art or can be prepared by techniques well known in the art. These polymers are prepared in general by free radical polymerization of one or more alkenyl azlactones, optionally with one or more free radically polymerizable, ethylenically unsaturated comonomers, using polymerization procedures common in the art. Suitable azlactone containing polymers and copolymers are described, for example, in R. Huebner, et al., *Angew. Makromol. Chem.*, 1970, 11, 109 and in U.S. Pat. No. 4,378,411. Particularly suitable azlactone-functional polymers for preparing coatings on solid supports can be prepared by reacting a portion of the azlactone groups of the above azlactone-containing homopolymers or copolymers with a lower alkyl amine or alcohol.

Other methods are available for preparing azlactone-functional polymeric supports. One method is to apply alkenyl azlactone monomer to the support (optionally along with other co-monomers) and polymerize the monomer(s) in place. Methods of polymerization include photopolymerization (utilizing an appropriate photoinitiator) as is well known in the art.

The azlactone-functional polymeric supports of have now been formed and are ready for reaction with a biologically active material which has "functional" group(s). "Functional" groups useful in the present invention include hydroxy, primary amine, secondary amine, and thiol. These groups react, either in the presence or absence of suitable catalysts, with azlactones by nucleophilic addition as depicted in equation (2) below.

wherein $R^1$, $R^2$, $R^3$, n, X, and G are as previously defined

Depending on the functional group present in the functional material, catalysts may be required to achieve effective attaching reaction rates. Primary amine functional groups require no catalysts. Acid catalysts such as trifluoroacetic acid, ethanesulfonic acid, toluenesulfonic acid, and the like are effective with hydroxy and secondary amine functional groups.

For the presently preferred azlactone-functional copolymeric bead, it is preferred to produce such beads according to Process II.

Biologically Active Materials

Azlactone groups will undergo nucleophilic attack by amines, thiols, and alcohols. Thus, biologically active materials having at least one amine, thiol, or alcohol group thereon are candidates for covalent immobilization on an azlactone-functional polymeric support.

Of the biologically active materials, proteins, enzymes and antigenic substances are desired for covalent immobilization. Nonlimiting examples of proteins, enzymes, and antigenic substances include natural and recombinant Protein A (ProtA), Immunoglobulins such as rat (rIgG), human (hIgG), bovine (bIgG), rabbit (rbIgG), and mouse (mIgG), Concanavalin A (ConA), Bovine Serum Albumin (BSA), Thyroglobulin (TG), Apoferritin (Af), Lysozyme (Ly), Carbonic Anhydrase (CA), and Bacterial Antigen (BA). Uses for immobilized proteins, enzymes and antigenic substances are disclosed in Heilmann et al.

The presently preferred biologically active material is ProtA because of its multitude of uses in bioseparations.

Polyanionic Salts

Inorganic Polyanionic Salts

Using an inorganic polyanionic salt in aqueous buffered media to covalently immobilize protein to azlactone-functional polymeric supports more than doubles the bound specific biological activity of the biologically active material, when compared to using an inorganic monoanionic salt, such as NaCl used in Heilmann et al.

This enhanced efficiency of immobilization is achieved in a very rapid and facile reaction. Unexpectedly, the use of an inorganic polyanionic salt in high concentrations does not disrupt other valued aspects of using azlactone-functional polymeric supports such as the very rapid covalent immobilization rates achievable at ambient temperatures.

Of the inorganic polyanionic salts, sulfates are desired because of increased bound specific biological activity relative to the molar concentration of inorganic polyanion in the aqueous media. Use of $Na_2SO_4$ is presently preferred when covalently immobilizing proteins (that have activity unaffected by metallic cations)in an aqueous medium buffered at a pH from about pH 4 to about pH 9. Sulfates are also preferred to phosphates because lower molar concentration of sulfates than phosphates is necessary to achieve the same density of covalently immobilized biologically active material on the azlactone-functional polymeric support and sulfates. Evidence of this advantage may be found in Coleman et al. *J. Chromatogr.* 512 (1990) 345-363, which is incorporated by reference herein.

Organic Polyanionic Salts

Organic polyacids and their salts can provide even more productive and efficient covalent immobilization of biologically active materials on azlactone-functional polymeric supports than inorganic polyanionic salts. Organic polyanionic salts are more consistently ionic than inorganic polyanionic salts in a pH range of pH 7 to pH 9 where most covalent immobilizations are conducted. Thus, organic polyanionic salts have a higher ionic strength per mole of polyanion. Consequently, fewer moles of organic salt are frequently required for covalent immobilization. Further, a greater variety of organic polyanionic salts than inorganic polyanionic salts is sufficiently soluble in buffered aqueous media employed in covalent immobilizations. Thus, organic polyanionic salts are presently preferred to inorganic polyanionic salts.

Of the organic polyacid candidates, di-acids, tri-acids, and tetra-acids, or their salts are desired. Nonlimiting examples of salts of such acids include malonate, malate, and tartrate di-acid salts of alkali metals, citrate tri-acid and nitrilo-tri-acetic acid (NTA) salts of alkali metals, and ethylenediaminetetraacetic acid (EDTA) tetra-acid salts of alkali metals. The presently preferred organic polyanionic salt is sodium citrate.

Aqueous Media and Amounts of Biologically Active Material, Polyanionic Salt and Buffering Agent Therein Biologically active material is dissolved or otherwise dispersed into a buffered aqueous medium.

Buffering agents for aqueous media include acetate, phosphate, pyrophosphate, borate, and others known to those skilled in the art, such as those buffering agents disclosed in Good et al., *Biochemistry*, 5, (1966) p. 467 et seq. (the disclosure of which is incorporated by reference herein).

The concentration of buffering agents in aqueous media can range from about 25 mM to about 750 mM and desirably from about 100 mM to about 500 mM. The presently preferred concentration of buffering agents can be between about 100 mM to about 500mM, inclusive, depending on the other concentrations of polyanionic salt and biologically active material chosen for covalent immobilization.

The concentration of polyanionic salt in aqueous buffered media can range from that amount which minimally useful to the limit of solubility of the salt in buffered medium. This range is also affected by the solubility limit of the biologically active material in aqueous media containing the polyanionic salt. For illustrative purposes only, whereas a 1.5M $Na_2SO_4$ concentration is acceptable for use with ProtA, a 0.75M concentration should be used with hIgG to prevent precipitation of the hIgG.

Desirably, the concentration of polyanionic salt for various aqueous buffered media can range from about 0.1M to about the solubility limit for a salt in a buffered medium, as much as 4M for $(NH_4)_2SO_4$, taking into consideration the solubility of the biologically active material.

The presently preferred concentration range of polyanionic salt useful in aqueous buffered media is from about 0.5M to at or near the solubility limit of a salt in a buffered aqueous medium.

The combination of buffering agent, polyanionic salt and water comprise a highly ionic buffered salt solution into which biologically active material is added.

The amount of biologically active material to be added to a highly ionic buffered salt solution chosen depends on the amount of biologically active material desired to be covalently immobilized on an azlactone-functional polymeric support and the bound specific biological activity of biologically active material desired. Because biologically active material is generally scarce and expensive, the density of biologically active material and the maximum bound specific biological activity possible determine the proper amount of biologically active material to be used for the present invention.

Broadly stated, biologically active material may be dissolved or otherwise dispersed in highly ionic buffered salt solution in an amount ranging from a minimally useful amount to the solubility limit of biologically active material in a highly ionic buffered salt solution.

Desirably, biologically active material is present in highly ionic buffered salt solution in an amount ranging from about 0.1 mg/ml of highly ionic buffered salt solution to at or near the solubility limit thereof.

The presently preferred amount of biologically active material in highly ionic buffered salt solution ranges from about 1 mg/ml of highly ionic buffered salt solution to about the solubility limit thereof.

The covalent immobilization of biologically active material in highly ionic buffered salt solution occurs within a pH range of from about pH 1 to about pH 13 and desirably from about pH 4 to about pH 11. Preferably, based on the preferred concentrations of buffering agent(s), polyanionic salt, and biologically active material, and the pH stability of biologically active material, the pH ranges from about pH 6 to about pH 9.

Method of Covalent Immobilization

In the first embodiment of the present invention, at least one inorganic polyanionic salt or at least one organic polyanionic salt and buffering agent comprise highly ionic buffered salt solution. Biologically active material is then added to form a biologically active material solution fully prepared for covalent immobilization, hereinafter called BAM solution.

In the second embodiment of the present invention, the same highly ionic buffered salt solution can be used. Both biologically active material and azlactone quencher are added to form a BAM-quencher solution.

In the first embodiment, a quantity of azlactone-functional polymeric support is mixed with the BAM solution under constant agitation for a period from about five minutes to about three hours at ambient temperature and pressure. Then azlactone quencher is added to the BAM solution to react with any remaining azlactone on the azlactone-functional polymeric support, followed by centrifuging, to remove solution, and repeating the quenching step.

In the second embodiment of the present invention, a quantity of azlactone-functional polymeric support is mixed with the BAM-quencher solution under the same conditions as in the first embodiment. Then as in the first embodiment, an azlactone quencher is added followed by centrifuging, separation, and re-quenching. Unexpectedly, the presence of the azlactone quencher in the BAM solution does not inactivate azlactone functionality of azlactone-functional polymeric support before optimized covalent immobilization of biologically active material to azlactone-functional polymeric support can occur.

Nonlimiting examples of azlactone quenchers for use in either embodiment include ethanolamine, bovine serum albumin, casein lysate, hydroxylamine, ethylamine, ammonium hydroxide, glycine, ammonium sulfate, butylamine, glycinamide, TRIS, gelatin, lysozyme, non-fat dry milk, beta-mercaptoethanol, mercaptoethylether, dithiothreitol, glutathione, arginine, guanidine, lysine, diamines, and combinations thereof. Some of these nonlimiting examples include proteins "irrelevant" to the immobilization desired. Alternatively, diverse, multiple activities on an azlactone-functional polymeric support can be achieved using two or more different biologically active materials.

For cost and handling, the use of ethanolamine as an azlactone quencher is presently preferred.

The concentration of azlactone quencher in highly ionic buffered salt solution of the second embodiment of the present invention ranges from about 0.1M to about 10M. Desirably, the range may be between about 0.5M to about 2M. When ethanolamine serves as azlactone quencher, the concentration may range from about 0.1M to about 1M. The presently preferred concentration of ethanolamine as azlactone quencher is about 0.5M to about 1M.

Usefulness of the Invention

When compared to covalent immobilization of biologically active materials disclosed in the art, including Heilmann et al., the present invention unexpectedly finds that bound specific biological activity of biologically active material on azlactone-functional supports is enhanced by the use of polyanionic salts in the aqueous media and, surprisingly, even more enhanced when the highly ionic buffered salt solution also contains azlactone quencher.

In a direct comparison between polyanionic salts of the present invention and physiological concentrations of buffered saline solution previously used by Heilmann et al. and others, the methods of the present invention improved bound specific biological activity by at least 13 percent and as much as 157 percent. When combined with the enhanced density of the immobilized biologically active material using polyanionic salts of the present invention compared with physiological concentrations of buffered saline solution previously used by Heilmann et al. and others, the capacity of the biologically active material for immobilized biologically active materials (amount of immobilized biologically active material multiplied by the bound specific biological activity) is at least double and as much as thirty-seven times the capacity achieved by Heilmann et al.

Alternatively, the use of the second embodiment of the present invention also improves capacity over the capacity achieved by Heilmann et al. Further, the capacity achieved by the use of the second embodiment of the present invention can exceed the capacity achieved by the use of the first embodiment of the present invention.

With either embodiment of the present invention, the method of covalent immobilization is very rapid. The reaction conditions are facile: ambient temperature and pressure. The methods are uncomplicated: either a two step process of covalent immobilization and quenching for the first embodiment or a combination of covalent immobilization and quenching for the second embodiment followed by further quenching.

A greater appreciation of the scope of the present invention is found in the following examples.

EXAMPLES

Method of Preparation of Azlactone-Functional Polymeric Supports and Biologically Active Materials Materials—Vinyldimethyl azlactone (VDM) was purchased from SNPE, Inc., Princeton, N.J. Methylene-bis-acrylamide (MBA) and all other organic reagents were obtained from Aldrich (Milwaukee, Wis.). Recombinant Protein A (rProtA) was purchased from Repligen (Cambridge, Mass.). The best available grades of the other proteins were purchased from Sigma Chemical (St. Louis, Mo.). Na$^{125}$I was purchased from Du Pont NEN (Billerica, Mass.). Iodo-beads and bicinchoninic acid reagents were purchased from Pierce Chemical (Rockford, Ill.).

Polymer Synthesis—The azlactone-functional polymeric support in the form of 20:80 VDM:MBA beads were prepared by inverse-phase polymerization (Process II) as follows:

Preparation of Copoly(Methylenebisacrylamide:2-Vinyl-4,4-dimethylazlactone) (20:80)

A 3-liter creased, round bottomed flask equipped with a mechanical stirrer (stirring rate 300 rpm), nitrogen inlet, thermometer, and condenser was charged in a solvent solution [(heptane (1043 mL) and carbon tetrachloride (565 mL) for Examples 1–5) and (ethyl acetate (1375 mL) and carbon tetrachloride (225 mL) for Examples 10–13) and (heptane (1043 mL) and toluene (565 mL) for the remaining Examples)] and stabilizer [( 4 grams of (90:10) copoly (isooctylacrylate:acrylic acid), sodium salt for Examples 1–5) and (4 grams of (91.8:8.2) copoly(isooctylacrylate: N-acryloyl- α-aminoisobutyramide for the remaining Examples))]. This solution was stirred and sparged with nitrogen for 15 minutes. A separate solution was prepared as follows: Methylenebisacrylamide (40 grams, 0.2549 mole) was dissolved in dimethylformamide (160 mL); after solution was achieved, water (160 mL) was added and the resulting solution sparged with nitrogen for 15 minutes. At this point, ammonium persulfate (1 gram) was added and sparging continued for 1 minute more. The solution was then quickly added to the organic suspending medium. Immediately following this addition, VDM (10 grams, 0.0719 mole) was added and the whole mixture was sparged for an additional 5 minutes. N,N,N',N'-tetramethyl-1,2-diaminoethane (2 mL) was added and the reaction temperature rose fairly rapidly from 22° to 29° C. The reaction mixture was stirred for a total of 4 hours from the time of the diamine addition, then filtered using a "D" (greater than 21 micrometers) sintered glass funnel. The filter cake was washed on the filter with acetone (2×500 mL), then dried at 60 degrees C and less than 1 torr until ready for use. IR analysis indicated a strong azlactone carbonyl absorption.

Protein Iodination—Proteins were radiolabeled with $^{125}$I by the chloramine-T reaction using Iodo-beads. The typical reaction contained 0.5 mg of protein (rProtA or rIgG) and 100 µCi of $^{125}$I-labeled sodium iodide in 100 mM sodium phosphate, 100 mM NaCl buffer (pH 7.5) and 2 Iodo-beads in a total volume of 500 µl. The reaction was terminated after 30–60 min by removal of the solution from the beads. Protein was separated from unreacted radioisotope on PD-10 columns (commercially available from Pharmacia). Typically 50% or more of the isotope was incorporated into the protein for a specific radioactivity of 0.10–0.15 µCi/µg of protein Radioiodinated protein solutions were stored frozen and used up to a month after preparation.

Protein Covalent Immobilization—The protein covalent immobilization reaction consisted of the mass polymeric beads indicated in Tables 1 and 3 suspended in volume of buffer identified in Tables 1 and 3, containing a variable amount of protein (20 µg to 5.0 mg). During immobilization the BAM solution was continuously rocked for the duration of the reaction at ambient temperature and pressure In comparative examples so indicated in the tables below, 150 mM NaCl (pH 7.5) was used. The remaining examples used either inorganic polyanionic salt or organic polyanionic salt identified in the tables. In examples 36–48, azlactone quencher was used during covalent immobilization. In all examples, after the indicated reaction time, the reaction was terminated by the addition of the azlactone quencher, 1.0M ethanolamine in 25 mM sodium pyrophosphate, which had been titrated to pH 9.0 with HCl.

After 5 min of continuous rocking, the sample was centrifuged, the supernatant solution was removed, and fresh ethanolamine solution was added to continue the quenching of the residual azlactone functional groups. After 60 min of additional reaction, the beads were centrifuged and resuspended several times in the pH 7.5 phosphate/NaCl buffer.

The amount of immobilized radiolabeled protein was determined in a Packard gamma scintillation counter (Model 5230). The specific radioactivity of the protein to be immobilized was adjusted prior to each experiment by addition of unlabeled protein and ranged from 100 to 2000 cpm/μg of protein. After the initial determination of immobilized radiolabeled protein, the amount which was covalently immobilized to the polymeric beads was determined following incubation of the beads with 1.0% sodium dodecylsulfate (SDS) for 4 hours at 37° C. with intermittent mixing, followed by centrifugation, removal of the supernate, and several additional wash cycles with SDS.

Activity of Immobilized rProtA Using Affinity Chromatography—Immobilized rProtA for affinity chromatography was prepared by 60-min reactions of the mass indicated in the Tables of 20:80 VDM:MBA beads with 1.25 to 25 mg of rProtA in a total volume indicated in the Tables of buffer at the indicated pH, containing the amount of salt shown in Tables 1 and 3. Residual azlactone functionality was inactivated by two treatments with ethanolamine, followed by washings with phosphate buffers and 1.0M NaCl to removed adsorbed protein. Derivatized beads were stored at 4° C. in 20% ethanol until used.

Chromatography was performed on a Pharmacia FPLC instrument controlled by the FPLC "Manager" software (Pharmacia).

Protein A affinity chromatography was performed with human serum (Examples 1–4) or with purified human hIgG (Examples 5 and 16–35) and either a 0.3×10-cm (0.70 ml) Omni column (Rainin, Woburn, Mass.) or a 0.5×10.0-cm (2.0 ml) column (Pharmacia). IgG was dissolved in 25 mM sodium phosphate, 150 mM NaCl (pH 7.5). The protein concentration and flow-rate varied according to the experiment. Human serum was diluted with an equal volume of the phosphate buffer. All samples were filtered through a 0.2-μm filter immediately prior to injection into the column. After the sample was loaded, the column was eluted first with the phosphate/NaCl buffer, followed in Examples 1–4 only by a step gradient to the same phosphate buffer with 1.0M NaCl, to remove any non-specifically bound protein, except where otherwise indicated. After the column was returned to the low-chloride buffer, the specifically bound IgG was eluted by a step gradient to 0.1M glycine/2.0% acetic acid buffer (pH 2.2). Recovery of protein from the column was determined by measurement of the absorbance at 280 nm of each fraction, since, at high protein concentrations (>2 mg/ml) the flow cell optical readings are unreliable. In these experiments, the stoichiometry of IgG: rProtA was calculated from the amount of radioactivity or absorbance at 280 nm eluted with the glycine treatment and 150,000 Da for the molecular weight and 1.3 cm$^2$/mg for the extinction coefficient of human IgG and 45,000 Da for rProtA.

Activity of Immobilized rProtA Using Immunoaffinity Chromatography

Immunoaffinity chromatography was conducted for Examples 10–15 as follows: Rat IgG (monoclonal antibody rIgG) was diluted in the indicated buffers (pH 8.0), with 3.0 mL of the resulting protein solution mixed with 150 mg azlactone beads for 60 minutes at room temperature. After centrifugation and removal of supernatant solution, 10.0 mL of 1.0M ethanolamine in 25 mM sodium pyrophosphate, pH 9.0, was added and allowed to react for 60 minutes. A second 10.0 ml amount of the quenching agent was subsequently added after centrifugation and removal of the first quencher addition. This second blocking action was allowed to incubate with continuous mixing at 4° C. overnight. The beads were rinsed for 30 minutes with each of the following solutions: 10 mL PBS, 10 Ml 1.0M NaCl, 10 mL PBS, 10 mL PBS, 10 mL 10 mM TRIS (twice). Beads were then stored at 4° C. until columns were packed. Beads were slurry packed in Omni glass columns (3 mm ID×5 cm), using 10 mM TRIS as the packing buffer. Mouse antigen was filtered and applied at a two-fold molar excess, loading in 10 mM TRIS, followed by equilibration to baseline, and elution in 0.1M glycine+ 2% acetic acid, pH 2.2. 1.0 mL fractions were collected, and antigen concentration was determined spectrophotometrically.

| | Glossary of terms used in Table 1–4. |
|---|---|
| rPA | recombinant Protein A commercially available from Repligen Corporation |
| fPA | Protein A commercially available from Fermentech |
| BSA | Bovine Serum albumin |
| NaCl | Sodium Chloride |
| BAM | Biologically Active Material |
| SO4 | Sodium sulfate |
| PO4 | Sodium Phosphate (monobasic sodium phosphate + dibasic sodium phosphate) |
| mIgG | mouse Immunoglobulin G |
| rIgG | rat IgG |
| hIgG | human IgG |
| MOPS | 3-[N-morpholino]propane-sulfonic acid |
| EDTA | sodium ethylenediamine-tetraacetic acid |
| EA | Ethanolamine |
| TR | TRIS (Tris[hydroxymethyl]aminomethane) |
| LiSO | Lithium sulfate |
| Citr | Sodium citrate |
| NH4 | Ammonium sulfate |

For Examples 1–35, the same method as described generally above was used, with the following exceptions: Bead mass, total volume, pH, and time are as indicated in Table 1. All immobilization reaction times were one hour. Quenching with ethanolamine was carried out for at least 6 hours, and typically overnight at 4° C. to ensure complete blockage of all residual reactive azlactone groups. Density of covalent immobilization of protein was determined by a simultaneous radiolabelled protein immobilization experiment.

TABLE 1

Conditions for Enhancement of Bound Specific Biological Activity by Inorganic Polyanionic Salts and Organic Polyanionic Salts

| Ex. | Bead Mass (mg) | BAM (mg/mL) | Buffer [M] | Salt [M] | T. Vol (ml) | pH |
|---|---|---|---|---|---|---|
| 1* | 250 | rPA (.25) | PO4 [.025] | NaCl [.15] | 5.00 | 7.5 |
| 2 | 250 | rPA (.25) | PO4 [.025] | SO4 [1.5] | 5.00 | 7.5 |
| 3* | 250 | rPA (5.0) | PO4 [.025] | NaCl [.15] | 5.00 | 7.5 |
| 4 | 250 | rPA (5.0) | PO4 [.025] | SO4 [1.5] | 5.00 | 7.5 |
| 5 | 250 | rPA (16.8) | PO4 [.025] | SO4 [1.5] | 5.00 | 7.5 |
| 6* | 50 | rPA (1.0) | PO4 [.025] | NaCl [.15] | 1.00 | 7.5 |
| 7 | 50 | rPA (0.1) | PO4 [.025] | SO4 [1.5] | 1.00 | 7.5 |
| 8* | 50 | rPA (10.0) | PO4 [.025] | NaCl [.15] | 1.00 | 7.5 |
| 9 | 50 | rPA (0.32) | PO4 [.025] | SO4 [1.5] | 1.00 | 7.5 |
| 10* | 150 | rIgG (1.0) | PO4 [.025] | NaCl [.15] | 3.0 | 8.0 |
| 11 | 150 | rIgG (1.0) | PO4 [.025] | SO4 [.75] | 3.0 | 8.0 |
| 12* | 150 | rIgG (6.4) | PO4 [.025] | NaCl [.15] | 3.0 | 8.0 |
| 13 | 150 | rIgG (6.4) | PO4 [.025] | SO4 [.75] | 3.0 | 8.0 |
| 14* | 50 | rIgG (2.6) | PO4 [.025] | NaCl [.15] | 1.0 | 7.5 |
| 15 | 50 | rIgG (1.0) | PO4 [.025] | SO4 [.75] | 1.0 | 7.5 |
| 16 | 50 | rPA (5.0) | PO4 [.25] | | 1.0 | 7.5 |
| 17 | 50 | rPA (5.0) | PO4 [.50] | SO4 [.25] | 1.0 | 7.5 |
| 18 | 50 | rPA (5.0) | PO4 [1.25] | | 1.0 | 7.5 |
| 19 | 50 | rPA (5.0) | PO4 [.50] | SO4 [.75] | 1.0 | 7.5 |
| 20 | 10 | fPA (5) | PO4 [.25](1) | | 0.2 | 7.5 |
| 21 | 10 | fPA (5) | PO4 [.50] | | 0.2 | 7.5 |
| 22 | 10 | fPA (5) | PO4 [.75] | | 0.2 | 7.5 |

TABLE 1-continued

Conditions for Enhancement of Bound Specific Biological Activity by Inorganic Polyanionic Salts and Organic Polyanionic Salts

| Ex. | Bead Mass (mg) | BAM (mg/mL) | Buffer [M] | Salt [M] | T. Vol (ml) | pH |
|---|---|---|---|---|---|---|
| 23 | 10 | fPA (5) | PO4 [1.0] | | 0.2 | 7.5 |
| 24 | 10 | fPA (5) | PO4 [1.25] | | 0.2 | 7.5 |
| 25 | 10 | fPA (5) | PO4 [1.50] | | 0.2 | 7.5 |
| 26 | 10 | fPA (5) | PO4 [2.00] | | 0.2 | 7.5 |
| 27* | 10 | fPA (5) | PO4 [.50] | SO4 [0] | 0.2 | 7.5 |
| 28 | 10 | fPA (5) | PO4 [.50] | SO4 [.25] | 0.2 | 7.5 |
| 29 | 10 | fPA (5) | PO4 [.50] | SO4 [.50] | 0.2 | 7.5 |
| 30 | 10 | fPA (5) | PO4 [.50] | SO4 [.75] | 0.2 | 7.5 |
| 31 | 10 | fPA (5) | PO4 [.50] | SO4 [1.0] | 0.2 | 7.5 |
| 32 | 10 | fPA (5) | PO4 [.50] | SO4 [1.25] | 0.2 | 7.5 |
| 33 | 10 | fPA (5) | PO4 [.50] | SO4 [1.50] | 0.2 | 7.5 |
| 34 | 50 | rPA (5.0) | MOPS [.50] | LiSO [1.50] | 1.0 | 7.5 |
| 35 | 50 | rPA (5.0) | PO4 [.5] | Citr [0.75] | 1.0 | 7.5 |

*Comparative Example
(1) In Examples 20-26, Buffer and Salt are merged in function.

TABLE 2

Results: Enhancement of Bound Specific Biological Activity by Inorganic Polyanionic Salts and Organic Polyanionic Salts

| | Immobilization Results | | Activity Results | |
|---|---|---|---|---|
| Ex. | BAM (mg/g) | Density (mg/ml) | Ratio (mol/mol) | Capacity (mg/ml) |
| 1* | 0.9 | 0.072 | 0.49 | 0.12 |
| 2 | 3.2 | 0.25 | 1.26 | 1.04 |
| 3* | 5.2 | 0.40 | 0.54 | 0.72 |
| 4 | 76.2 | 5.91 | 1.33 | 26.2 |
| 5 | 214.0 | 16.5 | 1.03 | 56.0 |
| 6* | 1.9 | 0.12 | 0.65 | |
| 7 | 1.7 | 0.10 | 0.97 | |
| 8* | 4.7 | 0.29 | 0.56 | |
| 9 | 4.5 | 0.28 | 0.95 | |
| 10* | 9.2 | 0.71 | 1.23 | 0.87 |
| 11 | 15.7 | 1.21 | 1.45 | 1.76 |
| 12* | 35.9 | 2.76 | 0.73 | 2.03 |
| 13 | 109.4 | 8.42 | 0.95 | 8.30 |
| 14* | 9.2 | 0.70 | 0.58 | |
| 15 | 10.4 | 0.65 | 0.66 | |
| 16 | 13.3 | 1.47 | 0.30 | 1.5 |
| 17 | 22.4 | 1.72 | 1.02 | 5.8 |
| 18 | 66.2 | 5.09 | 1.15 | 19.5 |
| 19 | 73.1 | 5.62 | 1.02 | 19.1 |
| 20 | 53.2 | 4.09 | 0.12 | 1.7 |
| 21 | 59.6 | 4.58 | — | — |
| 22 | 58.8 | 4.52 | — | — |
| 23 | 63.4 | 4.88 | — | — |
| 24 | 69.2 | 5.32 | 1.31 | 20.8 |
| 25 | 78.6 | 6.04 | — | — |
| 26 | 78.4 | 6.03 | — | — |
| 27 | 59.6 | 4.58 | — | — |
| 28 | 59.9 | 4.61 | 0.46 | 6.4 |
| 29 | 62.6 | 4.82 | — | — |
| 30 | 76.6 | 5.89 | 1.14 | 20.2 |
| 31 | 82.8 | 6.37 | — | — |
| 32 | 84.1 | 6.47 | — | — |
| 33 | 76.5 | 5.88 | — | — |
| 34 | 76.3 | 5.86 | 1.09 | 21.3 |
| 35 | 79.8 | 6.14 | 0.87 | 17.8 |

These examples, with comparative examples, demonstrate the unexpected finding that the addition of sulfate, phosphate, other inorganic polyanionic salt, or other organic polyanionic salt, or a combination of them to aqueous buffered media used to covalently immobilize proteins on azlactone bead supports enhances the bound specific biological activity of those proteins.

Examples 1 through 4 compare immobilization of rPA in the presence of 1.5M sodium sulfate and in the presence 0.15M sodium chloride The sulfate not only enhances the density of protein covalently immobilized, but also at least doubles the bound specific biological activity of the immobilized protein. The molar ratio of IgG eluted:immobilized rPA demonstrates that the immobilized rPA has been efficiently immobilized as compared to conventional techniques.

Example 5 shows that this enhancement of bound specific biological activity is independent of the density of rPA on the support, if given an excess of IgG to bind.

Examples 6 through 9 illustrate this enhancement of bound specific biological activity in sets of chromatography columns that had comparable density of immobilized ligand. rPA covalently immobilized on azlactone beads in the presence of 1.5M sodium sulfate shows enhanced bound specific biological activity, independent of density.

Examples 10 through 13 show enhanced bound specific biological activity also occurs with a different biologically active material, rat IgG, where the presence of 0.75M sulfate in Examples 11 and 13 resulted in greater bound specific biological activity of the immoblized antibody when tested with its specific antigen.

Examples 14 and 15 show enhanced bound specific biological activity for rat IgG, independent of the density of rat IgG covalently immobilized on the beads.

Examples 16 through 33 illustrate this observation for two different protein A products. Repligen protein A is a recombinant protein A of 45,000 da molecular weight, pI of 5.1. The Fermentech product has a molecular weight of 50,000. The Repligen product shows a slight increase in density of rPA covalently immobilized upon addition of sulfate at low concentration (Examples 16 and 17), but a 3-fold increase in bound specific biological activity (molar ratio). Using higher concentrations of polyanionic salts (Examples 18 and 19), the protein shows a 3-fold increase in density of immobilization compared to the results of Examples 16 and 17, and bound specific biological activity greater than the results of Example 16 but comparable to the results of Example 17.

Figure 1:
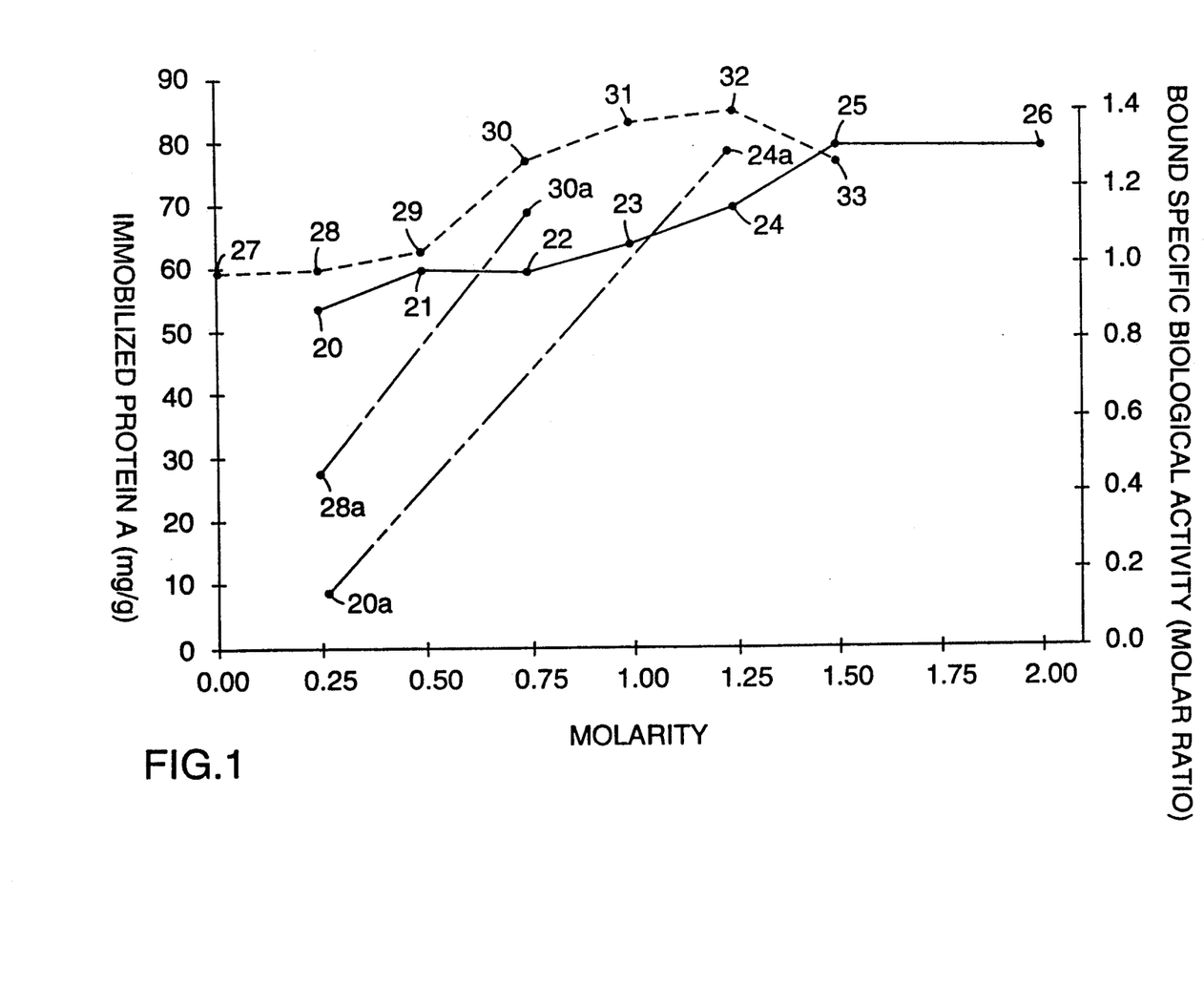
FIG. 1. is a graph of the amount of Protein A covalently immobilized in the presence of inorganic polyanionic salts and the bound specific biological activity achieved.

The Fermentech protein A (Examples 20 to 33), however, does not require the presence of high salt in the aqueous media to effect high density of covalent immobilization. FIG. 1 graphically shows the results of Examples 20-33. The results for Examples 20-26 shown in Table 2 are marked in FIG. 1 and show a density of covalent immobilization of biologically active material consistently above 50 mg/g. Yet the molar ratio expressing the bound specific biological activity bears no direct correlation. The bound specific biological activity for Example 20 (20a in FIG. 1) is much less than the bound specific biological activity for Example 24 (24a in FIG. 1.) Comparable results are obtained when sodium sulfate is used as the inorganic polyanionic salt. Compare Examples 28 and 30 shown as datapoints 28, 30, 28a, and 30a in FIG. 1. There is no direct correlation between density of immobilization achieved and amount of bound specific biological activity achieved. Thus, for efficiency of immobilization, a higher concentration of a polyanionic salt unexpectedly yields a higher bound specific biological activity. When combined with a higher density of immobilized biologically active material, the adduct support of azlactone-functional polymeric support and biologically active material is optimized.

The addition of either a high concentration of sulfate polyanion or a high concentration of phosphate polyanion increases the bound specific biological activity of the immobilized protein without a proportional increase in amount immobilized. Thus, achieving higher density of immobilization does not inherently yield a higher bound specific biological activity.

The enhancement of bound specific biological activity has also been observed with a differing cation (Example 34) and with an organic polyacid (Example 35), suggesting that the effect is not limited to the sodium cation, nor to the sulfate or phosphate anions.

EXAMPLES 36–48

Covalent Immobilization in the Presence of Azlactone Quencher rPA was immobilized onto the azlactone beads at the conditions indicated in Table 3. Immobilization reaction time in each example was one hour. Total volume of the solution in each example was one mL. Each preparation of beads was slurry-packed into an Omni glass column (3 mm ID×5 cm) and used for affinity chromatography as stated for Examples 1–35. hIgG at approximately 5 mg/mL was loaded onto each column in excess in PBS, pH 7.5, and eluted with the glycine/acetic acid buffer as stated above. Quantitation was done spectrophotometrically as above.

TABLE 3

Conditions: Activity of Protein Immobilized with Azlactone Quencher

| Ex. | Bead Mass (mg) | BAM (mg/ml) | Buffer [M] | Salt [M] | Amine [M] | T. Vol (ml) |
|---|---|---|---|---|---|---|
| 36 | 50 | rPA (5.0) | PO4 [.50] | SO4 [1.5] | | 1.0 |
| 37 | 50 | rPA (5.0) | PO4 [.50] | SO4 [1.5] | EA [0.1] | 1.0 |
| 38 | 50 | rPA (5.0) | PO4 [.50] | SO4 [1.5] | EA [1.0] | 1.0 |
| 39 | 50 | rPA (5.0) | PO4 [.50] | SO4 [1.5] | TR [0.5] | 1.0 |
| 40 | 50 | rPA (5.0) | | SO4 [1.5] | TR [0.5] | 1.0 |
| 41 | 50 | rPA (5.0) | MOPS [.5] | LiSO [1.5] | | 1.0 |
| 42 | 50 | rPA (5.0) | MOPS [.5] | LiSO [1.5] | EA [0.1] | 1.0 |
| 43 | 50 | rPA (5.0) | PO4 [.50] | Citr [.75] | | 1.0 |
| 44 | 50 | rPA (5.0) | PO4 [.50] | Citr [.75] | EA [1.0] | 1.0 |
| 45 | 50 | rPA (5.0) | PO4 [.50] | SO4 [1.5] | BSA[1] | 1.0 |
| 46 | 50 | rPA (5.0) | PO4 [.50] | SO4 [1.5] | BSA[2] | 1.0 |
| 47 | 50 | rPA (5.0) | PO4 [.50] | SO4 [1.5] | Casein[2] | 1.0 |
| 48 | 50 | rPA (5.0) | PO4 [.50] | SO4 [1.5][3] | NH4 [3][3] | 1.0 |

[1] 1 mg/ml
[2] 10 mg/ml
[3] Salt and Amine provided in the form of (NH4)2SO4

TABLE 4

Results: Activity of Second Embodiment

| | Immobilization Results | | Activity Results | |
|---|---|---|---|---|
| Ex. | BAM (mg/g) | Density (mg/ml) | Ratio | Capacity (mg/ml) |
| 36 | 90.3 | 6.95 | 0.62 | 14.4 |
| 37 | 90.7 | 6.73 | 0.75 | 16.8 |
| 38 | 75.2 | 5.78 | 0.95 | 18.3 |
| 39 | 88.3 | 6.79 | 0.70 | 15.8 |
| 40 | 81.6 | 6.28 | 1.08 | 22.7 |
| 41 | 76.3 | 5.86 | 1.09 | 21.3 |
| 42 | 43.3 | 3.34 | 1.49 | 16.6 |
| 43 | 79.8 | 6.14 | 0.87 | 17.8 |
| 44 | 68.6 | 5.28 | 1.14 | 20.0 |
| 45 | 91.6 | 7.05 | 0.66 | 15.5 |
| 46 | 91.9 | 7.07 | 0.59 | 14.0 |
| 47 | 92.6 | 7.12 | 0.59 | 14.0 |
| 48 | 23.4 | 1.80 | 2.04 | 12.2 |

The efficiency of the immobilized protein is demonstrated by the bound specific biological activity shown in Table 4. Indeed, both density of immobilization and bound specific biological activity are unexpectedly enhanced when compared to prior technologies and the results shown in Table 2.

In Examples 36 through 41, adding azlactone quencher at the time of covalent immobilization enhances both immobilization density and bound specific biological activity of the immobilized rPA. The azlactone quencher can be ethanolamine (Examples 36 through 38) or TRIS (Examples 39 and 40), mixed with the biologically active material, the buffering agent, and the polyanionic salt. Examples 41 and 42 also show the same unexpected results with lithium sulfate with and without ethamolamine as the azlactone quencher. The same is true for Examples 43 and 44 with sodium citrate with and without ethanolamine. Thus, any number of other inorganic salts and/or organic polyanionic salts may also confer these advantages on the immobilization process.

Use of larger amines, such as BSA, as azlactone quencher showed in Example 45 some improvement to bound specific biological activity as compared to NaCl salt immobilization and subsequent quenching described in Heilmann et al., if used as a concentration of 1 mg/mL or less Proteins at a concentration of 10 mg/mL (Examples 46 and 47) compare favorably with the conditions showed in Example 36. Example 48 shows that a single compound, ammonium sulfate, can be both the polyanionic salt and the azlactone quencher with excellent bound specific biological activity achieved.

Without being limited to the foregoing, the invention is hereby claimed.

What is claimed is:

1. A method for the covalent immobilization of biologically active material on azlactone-functional polymeric supports, comprising:
   (a) dissolving biomolecules and an azlactone quencher into a highly ionic buffered salt solution to form a biologically active solution, wherein the azlactone quencher has a concentration in the highly ionic buffered salt solution of at least about 0.1M; and
   (b) mixing said biologically active solution with azlactone-functional polymeric supports to form within three hours a biologically active adduct support with the biomolecules having a bound specific biological activity of at least ten percent greater than for the biomolecules immobilized on a biologically active adduct support using a buffered saline solution of a physiological concentration; said highly ionic buffered salt solution comprising a polyanionic salt having a concentration of from about 0.5M to about solubility limit of said polyanionic salt, wherein the biomolecules comprise biochemically, immunologically, physiologically, and/or pharmaceutically active molecules having at least one amine, thiol or alcohol group dissolved in the highly ionic buffered salt solution in a concentration from about 1.0 mg/ml to a concentration of about the solubility limit of the biomolecules in the highly ionic buffered salt solution.

2. The method according to claim 1, wherein said polyanionic salt is at least one inorganic polyanionic salt comprising sulfate, phosphates, pyrophosphates, pyrosulfates, arsenates, or borates.

3. The method according to claim 1, wherein said polyanionic salt is at least one organic polyanionic salt comprising citrates, tartrates, malonates, EDTA, or succinates.

4. The method according to claim 1, wherein the biomolecules comprise proteins, antibodies, antigens, enzymes, cofactors, lectins, hormones, receptors, coagulation factors, histones, cell surface antigens, or cell receptors.

5. The method according to claim 1, wherein the highly ionic buffered salt solution has a pH of from about pH 4 to pH 11.

6. The method according to claim 1, wherein the azlactone quencher comprises ethanolamine, bovine serum albumin, casein lysate, hydroxylamine, ethylamine, ammonium hydroxide, glycine, ammonium sulfate, butylamine, glycinamide, gelatin, lysozyme, nonfat dry milk, beta-mercaptoethanol, mercaptoethylether, dithiothreitol, glutathione, argimine, guanidine, lysine, diamines, Tris[hydroxymethyl]aminomethane, or combinations thereof.

7. The method according to claim 1, wherein the azlactone quencher has a concentration in the highly ionic buffered salt solution of from about 0.1M to about 10M.

8. A biologically active adduct support prepared from an azlactone-functional polymeric support and biomolecules covalently immobilized thereon in the presence of a highly ionic buffered salt solution using the method of claim 1 which yields a bound specific biological activity for the biomolecules of at least ten percent greater than for the biomolecules immobilized on a biologically active adduct support using a buffered saline solution in a physiological concentration,
wherein the biomolecules comprise biochemically, immunologically, physiologically, and/or pharmaceutically active molecules having at least one amine, thiol or alcohol group dissolved in the highly ionic buffered salt solution in a concentration from about 0.1 mg/ml to a concentration of about the solubility limit of the biomolecules in the highly ionic buffered salt solution.

9. The biologically active adduct support of claim 8, wherein the azlactone-functional polymeric support has units of the formula:

wherein
R$^1$ is H or CH$_3$,
R$^2$ and R$^3$ each independently is an alkyl group having 1 to 14 carbon atoms, a cycloalkyl group having 3 to 14 carbon atoms, an aryl group having 5 to 12 ring atoms, an arenyl group having 6 to 26 carbon and 0 to 3 S, N, and nonperoxidic O heteroatoms, or R$^2$ and R$^3$ taken together with the carbon to which they are joined can form a carbocyclic ring containing 4 to 12 ring atoms, and
n is an integer 0 or 1.

10. The biologically active adduct support according to claim 9, wherein the azlactone-functional polymeric support is crosslinked.

11. The biologically active adduct support according to claim 9, wherein the azlactone-functional biological support is a bead, membrane, film, or coating on a substrate.

12. The biologically active adduct support according to claim 9, wherein R$^1$ in the azlactone-functional polymeric support is hydrogen.

13. The biologically active adduct support according to claim 9, wherein R$^2$ and R$^3$ are methyl.

14. A biologically active adduct support having units of the formula wherein
R$^1$, R$^2$, R$^3$ and n are as previously defined in claim 2, n=0 or 1,
X is —O—, —S—, —NH—, or NR$^4$ wherein R$^4$ is alkyl or aryl, and
G is the residue of a biomolecule immobilized on the support in the presence of a highly ionic buffered salt solution using the method of claim 1 and has a bound specific biological activity for biomolecules of at least ten percent greater than for the biomolecules immobilized on a biologically active adduct support of said formula using a buffered saline solution of a physiological concentration,
wherein the biomolecules comprise biochemically, immunologically, physiologically, and/or pharmaceutically active molecules having at least one amine, thiol or alcohol group dissolved in the highly ionic buffered salt solution in a concentration from about 0.1 mg/ml to a concentration of about the solubility limit of the biomolecules in the highly ionic buffered salt solution.

15. The biologically active adduct support according to claim 14 wherein R$^1$ is hydrogen, R$^2$ and R$^3$ are methyl, and n=0.

16. The biologically active adduct support according to claim 14 wherein the support is a bead, a film, or a coating on a substrate.

* * * * *

UNITED STATES PATENT AND TRADEMARK OFFICE
CERTIFICATE OF CORRECTION

PATENT NO. : 5,200,471
DATED : April 6, 1993
INVENTOR(S) : Coleman et al.

It is certified that error appears in the above-identified patent and that said Letters Patent is hereby corrected as shown below:

Col. 7, lines 12-16, the formula should read

Col. 11, lines 21-28, the formula should read

UNITED STATES PATENT AND TRADEMARK OFFICE
CERTIFICATE OF CORRECTION

PATENT NO.  : 5,200,471
DATED       : April 6, 1993
INVENTOR(S) : Coleman et al.

It is certified that error appears in the above-identified patent and that said Letters Patent is hereby corrected as shown below:

Col. 16, line 3, "via" should read --<u>via</u>--.

Col. 17, line 13, "polymeric supports of have been formed" should read --polymeric supports have been formed--.

Col. 22, line 37, "protein Radioiodinated" should read --protein. Radioiodinated--.

Col. 22, line 47, "pressure In" should read --pressure. In--.

Col. 28, line 23, "less Proteins" should read --less. Proteins--.

Signed and Sealed this

Sixth Day of September, 1994

Attest:

BRUCE LEHMAN

*Attesting Officer*    *Commissioner of Patents and Trademarks*